United States Patent [19]

Miyamura et al.

[11] Patent Number: 6,063,904
[45] Date of Patent: May 16, 2000

[54] METHOD FOR PRODUCING ECTOPROTEIN OF HEPATITIS C VIRUS

[75] Inventors: Tatsuo Miyamura; Izumu Saito, both of Tokyo; Yoshiharu Matsuura, Kami-Fukuoka; Yoshikazu Honda, Kamakura; Makoto Seki, Machida, all of Japan

[73] Assignee: Japan as represented by the Director General of the Agency of National Institute of Health, Tokyo, Japan

[21] Appl. No.: 09/127,829

[22] Filed: Aug. 3, 1998

Related U.S. Application Data

[60] Continuation of application No. 08/462,195, Jun. 5, 1995, Pat. No. 5,789,544, which is a division of application No. 08/446,303, May 22, 1995, abandoned, which is a continuation of application No. 08/074,584, Jun. 11, 1993, abandoned.

[30] Foreign Application Priority Data

Jun. 11, 1992 [JP] Japan ..................................... 4-152487

[51] Int. Cl.⁷ .................................................... C07K 14/00
[52] U.S. Cl. ............................................................... 530/350
[58] Field of Search ........................... 530/350; 435/69.1, 435/69.3, 320.1; 536/23.72

[56] References Cited

U.S. PATENT DOCUMENTS

| 5,714,314 | 2/1998 | Miyamura et al. ...................... 435/5 |
| 5,734,019 | 3/1998 | Miyamura et al. ................... 530/350 |
| 5,747,241 | 5/1998 | Miyamura et al. ...................... 435/5 |
| 5,750,331 | 5/1998 | Miyamura et al. ...................... 435/5 |

*Primary Examiner*—Karen Cochrane Carlson
*Attorney, Agent, or Firm*—Oblon, Spivak, McClelland, Maier & Neustadt, P.C.

[57] ABSTRACT

A method for extracellularly producing an ectoprotein of hepatitis C virus comprises the steps of cultivating a transformant which is transformed with an expression vector containing a DNA fragment coding for the ectoprotein of hepatitis C virus and recovering the ectoprotein of hepatitis C virus extracellularly produced by the transformant. The protein originated from the E1 region prepared by the method can be used as a material for preparing a vaccine for preventing HCV infection. In addition, a diagnostic agent containing the protein is useful for the detection of an HCV antibody or the confirmation of the presence thereof in sera or the like. In other words, the protein of the present invention permits the diagnosis of C type hepatitis in high specificity and sensitivity.

5 Claims, 1 Drawing Sheet

FIG.1

METHOD FOR PRODUCING ECTOPROTEIN OF HEPATITIS C VIRUS

This application is a Continuation of application Ser. No. 08/462,195, filed on Jun. 5, 1995, U.S. Pat. No. 5,789,544 which is a Divisional of application Ser. No. 08/446,303, filed May 22, 1995, abandoned, which is a Continuation of Ser. No. 08/074,584, filed Jun. 11, 1993, now abandoned.

BACKGROUND OF THE INVENTION

The present invention relates to a method for producing an ectoprotein translated from the hepatitis C viral genome and more specifically to a method for producing a glycoprotein called first envelope protein (hereinafter referred to as "E1" protein) which is encoded by the hepatitis C virus (hereinafter referred to as "HCV") gene and which would be used as a material for preparing an HCV vaccine and as a diagnostic agent for detecting an anti-HCV envelope protein antibody.

In 1988, Chiron Co., Ltd. U.S.A. performed cloning of a novel human hepatitis virus conventionally called hepatitis non-A non-B virus and named it "HCV" and developed an agent for diagnosing C type hepatitis comprising a fused protein (C100-3) which is produced by a recombinant yeast cell transformed with a plasmid carrying a fragment of the HCV gene and a gene coding for human superoxide dismutase (SOD) and which is composed of a peptide encoded by the fragment of the HCV gene and human superoxide dismutase (SOD). The use of the diagnostic agent, accordingly, makes it clear that 71% of the post-transfusion hepatitis and 58% of the sporadic hepatitis are positive for the antibody (Science, 1989, 244, pp. 359–362 and pp. 362–364).

More specifically, it has been believed that the infection with C type hepatitis was caused by blood transfusion or the use of blood derivatives contaminated with the hepatitis virus, but it was proved that the crisis of sporadic C type hepatitis is also observed. This fact indicates, with emphasis, that immunization with a vaccine is effective for preventing infection with the C type hepatitis.

Thereafter, an HCV gene originated from a serum of a Japanese patient was cloned and correspondingly it became clear that the HCV prevailing in Japan was similar to that isolated by Chiron Co., Ltd., but was a strain peculiar to Japan comprising a quite different sequence (Tanpakushitsu Kakusan Koso (Proteins, Nucleic Acids and Enzymes). 1991, 36, pp. 1679–1691). However, the difference in antigenicity between the Japan strain and the U.S. strain has not yet been clarified. Moreover, the serotype of the HCV is believed to be only one irrespective of the diversity of the amino acid sequences thereof.

The foregoing C100-3 antibody-detecting system is proved to be insufficient in the rate of detection and detection sensitivity. For this reason, there have presently been used, as effective antigens for detection, mixtures of proteins such as proteins present in the core, NS3 and NS5 regions as diagnostic agents of secondary generation, but antibody-detecting systems for individual viral proteins have not yet been established at all. Therefore, there has been desired for the development of novel agents and methods for detecting or diagnosing HCV infection. Moreover, any vaccine for preventing infection with HCV and therapeutic agent for C type hepatitis have not yet been developed at all.

SUMMARY OF THE INVENTION

Accordingly, an object of the present invention is to provide a method for producing an ectoprotein translated from the hepatitis C viral genome.

Another object of the present invention is to provide a vaccine for preventing the crisis of C type hepatitis.

A further object of the present invention is to provide a novel diagnostic agent for detecting the infection with HCV.

As will be estimated from the observation on flavivirus and pestivirus which have gene structures similar to that of HCV, the HCV-infection phylactic antibody is assumed to be induced by the ectoprotein of HCV and further the ectoprotein is expected to be a novel diagnostic agent for evaluating conditions of C type hepatitis-infected patients through detection of the antibody against the protein. Thus, the foregoing objects of the present invention can be accomplished by the following method, in particular, by making host cells express a protein originated from the E1 region, preferably a protein produced, at a high rate, by an insect cell or an animal cell.

In general, the use of antigenic proteins present in the E1 region as materials for preparing vaccines and as diagnostic agents has been considered to be difficult since the proteins originated from the E1 region are cell membrane-bound glycoproteins and they suffer from such problems that the amount thereof expressed by a recombinant cell is very small and that the isolation and purification thereof from the protein-producing cells are very difficult. In fact, some of the inventors of this invention developed a method for making insect cells and animal cells express the gene cDNA coding for the protein, but it was proved that the production efficiency of the method was low and the purification of the resulting protein was very difficult (Journal of Virology, 1992, 66, pp. 1425–1431). Moreover, the inventors also tried to apply, to the production of the intended protein, the generally known method for improving the expression and purification efficiencies which comprises cutting the C-terminal anchor region of a membrane protein to make a host cell express the intended protein and extracellularly secrete the protein (Science, 1987, 238, pp. 1704–1707), but the method was found to be insufficient. Incidentally, the inventors of this invention have found out that the intended E1 protein is unexpectedly expressed and extracellularly secreted in high efficiency, when the cDNA from which the C-terminal anchor region and the central hydrophobic region present in the E1 region are deleted is expressed in insect cells or animal cells and thus have completed the present invention.

Accordingly, the foregoing object of the present invention can effectively be accomplished by a method for extracellularly producing an ectoprotein of hepatitis C virus comprising the steps of transforming a host with an expression vector containing a DNA fragment coding for the ectoprotein of hepatitis C virus, cultivating the transformant and recovering the ectoprotein of hepatitis C virus extracellularly produced by the transformant.

DESCRIPTION OF THE PREFERRED EMBODIMENTS

The present invention will hereinafter be explained in more detail.

The E1 protein of the present invention is a protein encoded by the HCV gene, i.e., a protein present in the region called the first ectoprotein and has an amino acid sequence corresponding to that shown in, for instance, Sequence ID No. 1 or 2 detailed in the attached Sequence Listing. The present invention, of course, includes proteins obtained by altering the amino acid sequence of the foregoing protein through deletion, insertion, modification or addition of a part of the amino acids thereof so far as their antigenicity against human and the reactivity with the sera from C type hepatitis-infected patients are not substantially impaired.

[1] Methods for Obtaining cDNA Clone Originated from C Type Hepatitis-infected Patients and Having the Base sequence of Sequence ID No. 1 Listed in Sequence Listing and Methods for Determining the Base Sequence of the Clone:

The E1 protein-coding gene having Base Sequence ID No. 1 of Sequence Listing or DNA fragments thereof can be obtained by, for instance, the following method.

The HCV is present in a serum in only a small amount and the gene thereof is RNA. Accordingly, it would be assumed to be difficult to clone the gene by the conventional methods for cloning cDNA's based on the Okayama-Berg method and the Gubler-Hoffman method. For this reason, the following method is adopted for certainly cloning the gene, extracted from a small amount of a serum, which easily undergoes mutation.

The nucleic acid is first extracted from a serum from a C type hepatitis-infected patient by the method shown in Example 1 described below. In general, the sera used in the invention are preferably those having OD values of not less than 3.5 as determined by an assay kit available from Ortho Company, but the present invention is not restricted to these specific sera. The serum is preferably admixed with a transfer RNA (tRNA) as a carrier for the viral RNA. The carrier is not restricted to tRNA's and any polyribonucleoside may be substituted for these tRNA's. In this respect, the use of a tRNA as such a carrier permits rapid confirmation of the presence or absence of a desired amount of the intact tRNA through electrophoresis and this confirmation in turn permits the confirmation of the presence of any decomposed viral RNA in any step subsequent to the step of mixing a tRNA as a carrier for the viral RNA with the serum. The polymerase chain reaction method (PCR method) developed by Saiki et al. (Nature, 1986, 324, p. 126) is preferably used as a means for cloning the cDNA starting from the nucleic acid thus extracted. First of all, the nucleic acid is reacted with a reverse transcriptase while using the viral RNA as a template. Primers used in this step may be any commercially available random primers or may be synthetic DNA's having base sequences such as primer AS1 having the following base sequence, Sequence ID No. 3:

Sequence ID No. 3 AS1: 5' CGGGATCCGG AGTAACT-GCG 3'

In each of the foregoing sequences, a different sequence may be substituted for a sequence having several bases on the 5' side, preferably not more than several bases in 10 bases on the 5' side and more preferably in 5 bases on the 5' side. In addition, 4 to 5 bases on the 5' side may be deleted and preferably several bases on the 5' side may be deleted. Moreover, any sequence may be added to the 5' end so far as the sequence comprises up to about 8 to 12, preferably up to 5 to 6 and more preferably up to several bases.

Specifically, the PCR method is carried out under the conditions detailed in Example 1. The PCR method is performed in the same manner used in Example 1 while using the first complementary DNA (1st cDNA) thus obtained as a template to give an intended DNA fragment.

In this case, the conditions for the PCR method can appropriately be selected depending on the situations. Specific sense primers usable herein are, for instance, those explained below:

Sequence ID No. 4 S1: 5' CGCTGCAGAC CGTGCATCAT GAGCAC 3'

In each of the foregoing sequences, a different sequence may be substituted for a sequence having several bases on the 5' side, preferably not more than several bases in 10 bases on the 5' side and more preferably in 5 bases on the 5' side. In addition, 4 to 5 bases on the 5' side may be deleted and preferably several bases on the 5' side may be deleted. Moreover, any sequence may be added to the 5' end so far as the sequence comprises up to about 8 to 12, preferably up to 5 to 6 and more preferably up to several bases.

The DNA fragment thus prepared is incorporated into one of cloning sites (e.g., Sma I site) of a cloning vector (for instance, pUC19) in the usual manner. The base sequences of both chains of the resulting clone are determined using a plasmid carrying the incorporated DNA fragment. The determination of the base sequences can easily be performed by the dideoxy method using, for instance, 7-Deaza Sequence Kit (available from Takara Shuzo Co., Ltd.) or Fluorescence Sequencer GENESIS 2000 available from Du-Pont Company according to the protocol of each kit. If there is a site whose sequencing is difficult and the DNA fragment to be sequenced comprises base pairs of not less than about 180, it is sufficient to subject them to sub-cloning in the usual manner. Sequence ID No. 1 of Sequence Listing represents the amino acid sequence of the protein estimated on the basis of the base sequence of the DNA fragment thus determined.

[2] Expression of the Polypeptide Encoded by the Clone Obtained in Step [1:]

If a desired clone is incorporated into an expression vector for *E. coli* or an eucaryote, the introduction of the clone into the vector is performed so as to be in accord with the frame of the initiation codon originated from the expression vector, while if any initiation codon derived from the vector is not used, the introduction of the clone into an expression vector is performed after an initiation codon is added to the 5' end so as to be in accord with the translation frame of the clone. The term "the translation frame of the clone" herein means each set of three successive bases in a base sequence, which corresponds to an amino acid, as will be apparent from, for instance, Sequence ID No. 1 of Sequence Listing which represents the base sequence of a representative clone.

The expression vector used in the present invention include a promoter at the position which permits the transcription of the DNA coding for the E1 protein originated from HCV which is obtained in the foregoing manner. For instance, if a microorganism such as *E. coli* or *Bacillus subtilis* is used as a host cell, the expression vector preferably comprises a promoter, ribosome binding sequence (SD sequence), a recombinant gene coding for the C type hepatitis-E1 protein originated from HCV, a transcription termination factor and a promote-regulating gene.

The promoters usable herein are those derived from microorganisms such as *E. coli* and bacteriophage and specific examples thereof include tryptophan synthetase (trp), lactose operon (lac), λ phages $P_L$ and $P_R$, and $T_5$ early gene $P_{25}$ and P26 promoters. Moreover, the promoters may be those having uniquely designed sequences.

The ribosome binding sequence may be those derived from *E. coli* and phages, but may likewise be those synthesized so as to have uniquely designed sequences and having consensus sequences comprising a sequence comprised of continuous not less than 4 bases complementary to the 3' terminal region of 16S ribosome RNA.

The transcription termination fact or is not an essential constituent, but the promoter desirably carries a ρ-independent transcription termination factor such as lipoprotein terminator and trp operon terminator.

In addition, these factors required for the expression are desirably arranged on the expression plasmid in the following order, starting from the 5' upstream side: the promoter, the SD sequence, the gene coding for E1 protein originated from HCV, the transcription termination factor.

The expression vector may be, for instance, commercially available pKK233-2 (Pharmacia Company). In addition, pGEX series (Pharmacia Company) may, for instance, be used as the expression vectors to make a host express the protein in the form of a fused protein.

The transformation of a host can be performed according to the protocol provided by Toyobo Co., Ltd. as will be detailed in Examples given below or by the usual manner.

Cultivation of the transformant thus obtained can be carried out in accordance with the method disclosed in Molecular Cloning, 1982. The cultivation is carried out at a temperature ranging from about 28 to about 42° C.

The production of the E1 protein requires appropriate selection of a host-vector system expressing the protein stably. More specifically, the expressed protein must have the intended biological activity, i.e., antigenicity identical to that of HCV. In particular, when taking into consideration the facts that the natural E1 protein is assumed to be a glycoprotein and that the E1 protein comprises a large number of cystein residues and the positions of thiol bonds formed between the cystein residues and the higher-order structure of the protein play an important role for the maintenance of the activity, the expression of the protein is performed using hosts, for instance, insect cells such as Sf9 cells and Sf21 cells with the Sf9 cells being preferred; and animal cells such as CHO cells, COS cells, mouse L cells, mouse C127 cells, mouse FM3A cells, with the CHO cells being preferred. Moreover, it is expected that an E1 protein subjected to processing can be produced by introducing, into a host cell, an E1 gene having a signal-like sequence in the amino acid sequence listed in Sequence Listing as Sequence ID No. 1, i.e., the amino acid sequence extending from 174th amino acid to 191th amino acid, if these cells are used as host cells. The expression plasmids for these insect or animal cells as host cells are constructed in the following manner:

Promoters are, for instance, multinuclear promoters (JIKKEN IGAKU (Experimental Medicine), 1990, 8 pp. 93–96) for insect cells; and promoters activated by adenovirus EIA gene (ZOKU SEIKAGAKU KOZA (Lectures on Biochemical Experiments, Second Series) 1, IDENSHI KENKYUHO (Methods for Gene Researches) 11, 1986, pp. 189–190), SV40 early promoter, SV40 late promoter, apolipoprotein E gene promoter, SR α promoter (Molecular and Cellular Biology, 1988. 8, pp. 466–472) for animal cells, with SV40 promoters or SR α promoter being preferred.

A DNA fragment of the gene coding for the E1 protein carrying the foregoing signal-like sequence is inserted into the downstream of the promoter along the direction of the transcription. In the construction of the E1 protein-expressing vector, not less than two fractions of the gene coding for the E1 protein linked together may be inserted into the downsteam of the promoter. Alternatively, it is also possible to insert, into the vector, not less than two units of DNA fragments linked together while arranging the directions of transcription, the DNA fragments each comprising a DNA fragment of the gene coding for the E1 protein and a promoter such as SV40 linked to the 5' upstream side of the fragment. This gene coding for the E1 protein requires a polyadenylated sequence at the downstream thereof. For instance, one polyadenylated sequence derived from SV40 gene, β-globin gene or metallothionein gene must be present in the downstream of the gene coding for the E1 protein. When linking not less than two DNA fragments, each comprising a DNA fragment of the gene coding for the E1 protein and a promoter, each unit of the DNA fragment may comprise a polyadenylated sequence on the 3' side of the gene coding for the E1 protein.

When transforming an animal cell such as a CHO cell with this expression vector, a selective marker is desirably used. Examples of such selective markers include DBFR gene for imparting methotrexate-resistance to the mammalian cell (Journal of Molecular Biology, 1982, 159, p. 601), Neo gene for imparting antibiotic G-418-resistance to the cell (Journal of Molecular Applied Genetics, 1982, 1, p. 327), Ecogpt gene originated from E. coli for imparting mycophenol-resistaince thereto (Proceedings of the National Academy of Sciences of the USA, 1981, 78, p. 2072) and hph gene for imparting antibiotic hygromycin-resistance thereto (Molecular and Cellular Biology, 1985, 5, p. 410). A promoter such as the promoter originated from the foregoing SV40 or TK gene promoter of herpesvirus is inserted into the 5' upstream side of each resistant gene and the resistant gene comprises the foregoing polyadenylated sequence in the 3' downstream side thereof. These resistant genes may be inserted into the E1 protein-expression vector in the right or opposite orientation in the downstream of the polyadenylated site of the gene coding for the E1 protein. The use of these expression vectors eliminates the need for double transformation of another plasmid containing a selective marker gene upon constructing the transformant.

If these selective markers are not inserted into the E1 protein-expression vector, a host cell can be subjected to double transformation with an expression vector for the gene coding for the E1 protein and a vector carrying a selective marker for the resulting transformant such as pSV2neo (Journal of Molecular Applied Genetics, 1982, 1, p. 327), pMBG (Nature, 1981, 294, p. 228), pSV2gpt (Proceedings of the National Academy of Sciences of the USA, 1981, 78, p. 2072) or pAD-D26-l (Journal of Molecular Biology, 1982, 159, p. 601). Thus, a desired transformant can easily be selected on the basis of the phenotype of the selective marker gene.

The expression vector is introduced into an insect or animal cell by, for instance, the calcium phosphate technique (Virology, 1973, 52, p. 456) and the electroporation technique (Journal of Membrane Biology, 1972, 10, p. 279), with the calcium phosphate technique being generally adopted.

The transformed cell can be cultured by the usual manner such as the suspension culture and the adhesion culture. The cultivation is performed in a culture medium such as Grace's culture medium, MEM and Ham F-12 in the presence of 5 to 10% serum or a proper amount of insulin, dexamethasone and/or transferrin or in the absence of any serum. The cells expressing the E1 protein are detected by commonly used fluorescent antibody technique using, for instance, a patient's serum and cloned by the commonly used limiting dilution-culture method to thus establish a cell line which stably produces the E1 protein.

The E1 protein originated from the HCV gene thus obtained can be used as a vaccine in the form of a mixture with, for instance, adjuvants or as an HCV antigen for use in diagnosis of HCV infection. The antigen which immunologically reacts with an HCV antibody-containing serum is useful for the detect ion of the HCV antibody or the confirmation of the presence thereof in sera. Examples of such immunoassay methods include RIA (radioimmunoassay), ELISA (enzyme-linked immunoadsorbent assay), fluorescent antibody technique, agglutination reaction (inclusive of latex method) and immunoprecipitation method. In most cases, labeled-antibodies are used in the detection. In this case, the antibodies are labeled with, for instance, fluorescent substances, chemiluminescent substances, radioactive substances and staining substances. Thus, the E1 protein originated from the HCV gene, which serves as an antigen, can be used for preparing a vaccine for preventing the HCV infection or can be used as an immunological diagnostic agent effectively used for, for instance, estimating the therapeutic effect.

The protein originated from the E1 region prepared by the method of the present invention can be used as a material for preparing a vaccine for preventing the HCV infection. In addition, a diagnostic agent containing the protein is useful for the detection of the HCV antibody or the confirmation of the presence thereof in sera or the like. In other words, the protein of the present invention permits the diagnosis of C type hepatitis in high specificity and sensitivity.

The present invention will hereinafter be explained in more detail with reference to the following working Examples, but the present invention is not restricted to these specific Examples.

EXAMPLE 1

[1] Extraction of Nucleic Acid from Sera Collected from HCV-infected Patients

To 10 ml of a serum obtained from a patient suffering from C type hepatitis (the serum had an OD value of not less than 3.5 as determined by HCV EIA Kit available from Ortho Company), there was added 25 ml of Tris-buffer (50 mM Tris-HCl, pH 8.0, 1 mM EDTA, 100 mM NaCl), followed by admixing, centrifugation at 20,000 g and 20° C. for 20 minutes and additional centrifugation of the resulting supernatant at 100,000 g and 20° C. for 5 hours. To the resulting precipitates, there was added 1.5 ml of a protenase K solution (1% sodium dodecylsulfate, 10 mM EDTA, 10 mM Tris-HCl, pH 7.5, 2 mg/ml Protenase K (available from Sigma Company), 6.6 μg yeast tRNA mixture). After dissolution of the precipitates, the solution was maintained at 45° C. for 90 minutes and then so-called phenol/chloroform treatment was repeated four times or more, the phenol/chloroform treatment comprising adding an equal volume of phenol/chloroform to the solution, vigorously mixing and then recovering an aqueous phase containing nucleic acids through centrifugation. The aqueous phase was subjected to chloroform treatment over two times or more. To the aqueous phase thus obtained, there were added a 3M sodium acetate solution in a volume of 1/10 time that of the aqueous phase or an equal volume of a 4M ammonium acetate solution and ethanol in a volume of 2.5 times that of the aqueous phase, the resulting mixture was stirred, allowed to stand at −20° C. overnight or at −80° C. for not less than 15 minutes and then subjected to centrifugation at 35,000 rpm for 4 hours using SW41 Ti rotor (available from Beckman Company) to recover the nucleic acid in the form of precipitates.

[2] Synthesis of cDNA

[2-1] Preparation of RNA Sample

After drying the nucleic acid obtained in the step [1]. 30 μl of water and 10 μl of a ribonuclease-inhibitor solution (100 unit/μl. available from Takara Shuzo Co., Ltd.) were added to the dried nucleic acid to dissolve it. This aqueous solution of the nucleic acid was used in the preparation of cDNA detailed below.

[2-2] Synthesis of cDNA Using Antisense Primer

To 2 μl of the aqueous nucleic acid solution prepared in the step [2-1], there were added 1 82 l of an antisense primer (synthetic DNA primer AS1) solution (15 pmols/μl), 2 μl of 10×RT buffer (100 mM Tris-HCl, pH 8.3, 500 mM KCl), 4 μl of a 25 mM $MgCl_2$ solution, 8 μl of a 2.5 mM 4dNTP solution and 1 μl of water. After allowing the mixture to stand at 65° C. for 5 minutes and then at room temperature for 5 minutes, there were added, to the mixture, 1 μl of a reverse transcriptase (available from Life Science Company, 25 units) and 1 μl of a ribonuclease-inhibitor (100 unit/μl, available from Takara Shuzo Co., Ltd.), then the mixture was allowed to stand at 37° C. for 20 minutes. then at 42° C. for 30 minutes and finally at 95° C. for 2 minutes and immediately thereafter it was cooled to 0° C. (synthesis of a complementary DNA). A 10 μl volume of the DNA sample was used and DNA's having specific sequences present therein were amplified by the so-called PCR technique performed according to the method of Saiki et al. (Nature, 1986, 324, p. 126).

More specifically, the DNA sample (10 μl) was mixed with 10×PCR buffer (100 mM Tris-HCl, pH 8.3, 500 mM KCl, 15 mM $MgCl_2$), 10 μl of a 1% gelatin solution, 8 μl of a 2.5 mM 4dNTP solution, 2 μl of the synthetic DNA primer solution used above in the synthesis of the cDNA (150 pmols/μl), 3 μl of a synthetic DNA primer corresponding to the foregoing primer (15 pmols/μl; the counterpart of the synthetic DNA primer used above in the synthesis of the cDNA (in this case, aforementioned primer S1)) and water was then added to the mixture in such an amount that the total volume of the mixture reached 100 μl. The mixture was allowed to stand at 95° C. for 5 minutes and then quenched down to 0° C. After one minute, 0.5 μl of a Taq DNA polymerase solution (7 units/μl; AmpliTaq TM, available from Takara Shuzo Co., Ltd.) was added to and mixed with the foregoing mixture and then a mineral oil was layered on the top of the sample. This sample was treated in DNA Thermal Cycler available from Perkin Elmer Cetus Company over 25 cycles, each cycle comprising treatments at 95° C. for one minute, at 40 to 55° C. for one minute and 72° C. for 1 to 5 minutes. Finally, the sample was maintained at 72° C. for 7 minutes, then the aqueous reaction solution was subjected to a phenol/chloroform treatment and an ethanol precipitation treatment (this treatment comprised the steps of adding a 3M sodium acetate solution in a volume of 1/10 time that of the aqueous phase or an equal volume of a 4M ammonium acetate solution and ethanol in a volume of 2.5 times that of the aqueous phase, mixing these components, centrifuging at 15,000 rpm and 4° C. for 15 minutes using a rotor having a radius of about 5 cm and then drying the resulting precipitates) to thus give amplified DNA fragments.

[3] Cloning and Sequencing of the Amplified DNA Fragment

At least 1 pmole of the DNA fragment obtained in the step [2-2] was digested with restriction enzymes Pst I and Bam HI (available from Toyobo Co., Ltd.), then subjected to a phenol/chloroform treatment and an ethanol precipitation treatment and incorporated into pUC19 cloning vector present within the multicloning site and digested with restriction enzymes Pst I and Bam HI using Ligation Kit (available from Takara Shuzo Co., Ltd.).

The vector DNA used in the ligation was prepared as follows and used in an amount of 5 to 10 ng. In other words, the pUC19 cloning vector was cleaved with restriction enzymes Pst I and Bam HI (available from Toyobo Co., Ltd.), subjected to a phenol/chloroform treatment and an ethanol precipitation treatment, followed by dephosphorylation of the 5' end thereof with alkaliphosphatase (available from Boehlinger Mannheim Company) (Molecular Cloning, 1982, Cold Spring Harbor Lab. Press), a phenol/chloroform treatment and an ethanol precipitation treatment.

The DNA thus prepared was used for the transformation of *E. coli* JM109 (at this stage, a competent cell used is available from Toyobo Co., Ld.). The transformation was performed according to the protocol for COMPETENT HIGH available from Toyobo Co., Ltd. In this way, at least 20 transformants were obtained, which were transformed with pUC19 cloning vector carrying the DNA fragment which was obtained using the foregoing combination of primers according to the method [2-2].

A plasmid DNA was prepared from one of the transformants thus formed (pUC010), then a deletion mutant thereof was produced using Deletion Kit (available from Takara Shuzo Co., Ltd.) in accordance with the protocol thereof and the mutant was sequenced in the usual manner using 7-Deaza Sequence Kit (Takara Shuzo Co., Ltd.) or Fluorescence Sequencer GENESIS 2000 System (Du-Pont Company). The base sequences of the + and − strands of the DNA fragment were determined using two synthetic primers having the following sequences (Sequence ID No. 5 and Sequence ID No. 6) as sequence primers:
Sequence ID No. 5 5' d(GTAAAACGACGGCCAGT) 3'
Sequence ID No. 6 5' d(CAGGAAACAGCTATGAC) 3'
The DNA fragment has a base sequence identical to that represented by Sequence ID No. 1 shown in Sequence Listing. The amino acid sequence represented by Sequence ID No. 1 shown in Sequence Listing is encoded in the + strand of the HCV-derived gene incorporated into the plasmid of the transformant constructed above.

[4] Modification of Gene Coding for E1 Protein

The E1 protein-coding gene was modified in the following manner to make the DNA fragment included in the plasmid constructed in the step [3] express and to achieve secretion thereof in high efficiency.

First, 1 μg of the plasmid constructed in the step [3] was digested with a restriction enzyme Dra III (New England, Bio-Lab Company), then partially digested with a restriction enzyme Hgi AI and subjected to a phenol/chloroform treatment and an ethanol precipitation treatment. A synthetic linker (5 ng) having a base sequence represented by the following Sequence ID No. 7 was inserted into the DNA (10 ng) thus prepared using Ligation Kit (Takara Shuzo Co., Ltd.):
Sequence ID No. 7 5' d(AGCGGCCGCT) 3'
*E. coli* DH5 was transformed with the DNA thus obtained (at this stage, there was used a competent cell available from Toyobo Co., Ld.). The transformation was performed according to the protocol for COMPETENT HIGH available from Toyobo Co., Ltd. The recombinants thus obtained were subjected to a miniscreening process performed by the usual manner (Molecular Cloning, 1982, Cold Spring Harbor Lab. Press) to give a plasmid pUC813 in which the foregoing synthetic linker was incorporated into the E1 gene thereof.

Then 1 μg of the DNA thus produced was digested with a restriction enzyme HincII, followed by partial digestion with a restriction enzyme Pvu II, a phenol/chloroform treatment and an ethanol precipitation treatment. The DNA (5 ng) thus obtained was ligated using Ligation Kit (available from Takara Shuzo Co., Ltd.) and *E. coli* DH5 cells were transformed with the DNA (at this stage, there was used a competent cell available from Toyobo Co., Ltd.). The transformation was performed according to the protocol of COMPETENT HIGH available from Toyobo Co., Ltd. The recombinants thus obtained were subjected to miniscreening performed by the usual manner (Molecular Cloning, 1982, Cold Spring Harbor Lab. Press) to give a plasmid pUC813d in which the Pvu II site in the vector was not cleaved, but the PvuII site in the E1 protein-coding gene was cleaved.

[5] Expression of E1 Protein in Insect Cells

To make an insect cell express the modified E1 protein encoded by the plasmid pUC813d constructed in the step [4], the fragments of the plasmid pUC813d cleaved with restriction enzymes Not I and Bam HI were inserted into the sites of a transfer vector pAc813 constructed by Matsuura et al. (a transfer vector which carries unmodified E1 protein-coding gene inserted therein disclosed in Journal of Virology, 1992, 66, pp. 1425–1431, available from National Institute of Health) cleaved with restriction enzymes Not I and Bam HI respectively (Ligation Kit available from Takara Shuzo Co., Ltd. was used for the ligation in accordance with the protocol of the Ligation Kit), then *E. coli* DH5 cells were transformed using the resulting DNA and the recombinants thus obtained were subjected to miniscreening to give a desired plasmid. The resulting plasmid was isolated from the recombinant *E. coli* cells and purified by the method of Maniatis et al. (Molecular Cloning, 1982, pp. 86–96, Cold Spring Harbor Lab. Press) to give a large quantity of an HCV-modified E1 gene transfer plasmid (pAc813d) DNA. The plasmid DNA (12.5 μg) thus obtained and a virus (AcNPV) DNA (1 μg) were admixed with a transfection buffer (20 mM HEPES, 1 mM $Na_2HPO_4$, 5 mM KCl, 140 mM NaCl, 10 mM glucose. pH 7.05; 750 μl) and diluted with distilled water to a final volume of 950 μl. To the mixture, there was dropwise added 50 μl of a 2.5M $CaCl_2$ while stirring the tube for the addition and then the mixture was allowed to stand at room temperature for 30 minutes to form precipitates. The precipitates were lightly disintegrated through tipping and then Sf9 cells were transformed. More specifically, the Sf9 cells were cultured in a Grace's culture medium (available from GIBCO Company) contained in a Petri dish, to which 10% FCS (fetal calf serum) was supplemented till the number of the cells reached $1 \times 10^6$/Petri dish.

Then the culture medium was removed from the Petri dish, 0.95 ml of a transfection buffer mixed with the foregoing DNA was added thereto, followed by allowing it to stand at room temperature for one hour, removal of the DNA-containing liquid, addition of 2 ml of a Grace's culture medium containing 10% FCS to the Petri dish and cultivation at 27° C. for 6 days. In this respect, some cells were converted into multinucleate cells on 3rd day of the cultivation and almost all cells were converted into multinucleate cells on 6th day thereof. The supernatant of the culture medium was collected in a centrifuge tube and centrifuged at 1,000 rpm for 10 minutes. The resulting supernatant was used as coinfection-viral liquid.

This coinfection-viral liquid comprises $10^8$ viruses/ml and the content of recombinants is about 0.5% thereof. The plaque-isolation technique detailed below was used for the isolation of the recombinant viruses. The coinfection-viral liquid was first diluted $10^4$ and $10^5$ times. After cells ($1.5 \times 10^6$ cells/Petri dish) were inoculated into culture mediums included in Petri dishes having diameters of 6 cm and adhered to the dishes and the culture medium was removed, the coinfection-viral liquids diluted $10^4$ and $10^5$ times respectively (100 μl each/Petri dish) were added to each of Petri dishes. These Petri dishes were inclined at intervals of 15 minutes such that the viral liquid spread over the whole surface of the Petri dishes in order to prevent the drying of the cells. In this way, the cells were infected with the viruses at room temperature for one hour. Separately, 3% Sea Plaque Agarose (available from Takara Shuzo Co., Ltd.) was mixed with Grace's culture medium containing 10% FCS, which had been treated at 105° C. for 10 minutes in an autoclave and then was maintained at 46° C. in a ratio of 1:2 and the resulting mixture was maintained at 46° C.

After completion of the infection, the viral liquid was completely removed and a warmed piled up agar medium (2 ml/Petri dish) was gently added while taking precautions to prevent any peeling off of the cells. The cells were allowed to stand while slightly shifting the covers of the Petri dishes till the agarose was solidified and dried and then 1 ml of Grace's culture medium supplemented with 10% FCS was layered on the top of the solidified agarose layer, followed by incubation thereof at 27° C. After the cultivation over 4 days, the cells were subjected to supravital staining with Neutral Red (Nakarai Tesk Co., Ltd.) and observed under a phase contrast microscope to detect plaques which were free of apocyte-formation. The plaque free of apocyte-formation was aspirated together with the agarose using a Pasteur pipet and pipetted in 1 ml of a Grace's culture medium to suspend the recombinant viral cells in the medium. A series of the foregoing operations (the operation for infection, the cultivation over 4 days and isolation of the recombinant viral cells) is called plaque-purification technique. The virus suspension (100 $\mu$l) was taken and subjected to plaque purification identical to that performed above. A series of these operations was repeated three times to give a recombinant virus Ac813d carrying HCV-derived E1 protein-coding gene and free of contamination with wild strains.

To produce the modified E1 protein, $5 \times 10^6$ Sf9 cells were previously suspended in 10 ml of a Grace's culture medium supplemented with 10% FCS, inoculated in a culture medium-containing Petri dish having a diameter of 10 cm, followed by allowing to stand for one hour to adhere the cells to the Petri dish. The culture medium was removed from the Petri dish, 250 $\mu$l of an Ac813d virus-containing solution was added to and spread over the Petri dish, followed by addition of 10 ml of a 10% FCS-containing Grace's culture medium thereto and cultivation thereof at 27° C. for 4 days to thus make the HCV-infected Sf9 cells express the HCV-derived E1 glycoprotein extracellularly.

[6] Expression of E1 Protein in Animal Cells

To make an animal cell express the modified E1 protein encoded by the plasmid pUC813d constructed in the step [4], the fragments of the plasmid pUC813d cleaved with restriction enzymes Not I and Bam HI were inserted into the sites of an expression vector pSR816X constructed by Matsuura et al. (an animal cell-expression vector which carries unmodified E1 protein-coding gene inserted therein disclosed in Journal of Virology, 1992, 66, pp. 1425–1431, available from National Institute of Health) cleaved with restriction enzymes Not I and Bam HI (Bam HI partially digested the vector) respectively, then *E. coli* DH5 cells were transformed using the resulting DNA and the transformants thus obtained were subjected to a miniscreening process to give a desired plasmid. The resulting plasmid was isolated from the recombinant *E. coli* cells and purified by the method of Maniatis et al. (Molecular Cloning, 1982, pp. 86–96, Cold Spring Harbor Lab. Press) to give a large quantity of an HCV-modified E1 gene-expression plasmid (pSR813dXDNA).

The plasmid pSR813dXDNA thus obtained in the step [6] was used for transforming CHO cells through the transfection of CHO cells on the basis of the method of Ausubel et al. (Current Protocols in Molecular Biology, Green Publishing Associates and Wiley-Interscience, 1987, §9 .1.1 to §9.1.4).

More specifically, CHO cells were cultured in a Petri dish of 6 cm diameter containing a Ham F-12 culture medium (available from GIBCO Company) supplemented with 10% FCS (fetal calf serum) till the CHO cells reached semiconfluent growth state. Then the culture medium was removed from the Petri dish and a solution containing the foregoing DNA was dropwise added. In this respect, the DNA solution was, in advance, prepared as follows. To each Petri dish having a diameter of 6 cm, there were added 300 $\mu$l of a 2×HEBS solution (2×HEBS solution: 1.6% NaCl, 0.074% KCl, 0.05% $NaH_2PO_4.12H_2O$, 0.2% dextrose, 1% HEPES, pH 7.05) and 10 $\mu$g of the plasmid DNA, then sterilized water was added to the total volume of 570 $\mu$l and the resulting solution was introduced into an Eppendorf centrifuge tube. To the DNA solution, there was then dropwise added 30 $\mu$l of a 2.5M calcium chloride solution while vigorously stirring for 1 to 2 seconds in a vortex mixer. The resulting mixture was allowed to stand at room temperature for 30 minutes, while stirring it in a vortex mixer at intervals of about 10 minutes. The DNA solution thus prepared was sprayed on the foregoing cells and the cells were allowed to stand at room temperature over 30 minutes. Thereafter, 5 ml of a Ham F-12 culture medium (GIBCO Company) supplemented with 10% FCS was added to the Petri dish and the cells were cultured at 37° C. for 4 to 5 hours in the presence of 5% $CO_2$. Then the culture medium was removed from the Petri dish, the cells were washed with 5 ml of a $TBS^{++}$ solution (25mM Tris-HCl, pH 7.5, 140 mM NaCl, 5 mM KCl, 0.6 mM $NaH_2PO_4$, 0.08 mM $CaCl_2$, 0.08 mM $MgCl_2$), then the $TBS^{++}$ solution was removed, a $TBS^{++}$ solution supplemented with 20% glycerol was sprayed on the cells, the cells were allowed to stand at room temperature for 1 to 2 minutes, followed by removal of the resulting supernatant. Thereafter, the cells were again washed with 5 ml of a $TBS^{++}$ solution, followed by addition of 10% FCS-containing Ham F-12 culture medium to the Petri dish, cultivation of the cells at 37° C. in the presence of 5% $C\mathbf{0}_2$, removal of the culture medium 48 hours after the initiation of the cultivation, washing of the cells with 5 ml of a $TBS^{++}$ solution, spray of 1 ml of a trypsin-EDTA solution (Sigma Company) on the cells and allowing to stand at room temperature for 30 seconds. Thereafter, the trypsin-EDTA solution was removed, the cells were dispersed by addition of 5 ml of a 10% FCS-containing Ham F-12 culture medium to the Petri dish 5 minutes after the removal, followed by counting up the number of cells, spread of the cells on 96-well microplates in populations of 0.5 cell/well/100 $\mu$l, 1 cell/well/100 $\mu$l, 2 cells/well/100 $\mu$l, 4 cells/well/100 $\mu$l and 8 cells/well/100 $\mu$l respectively and addition of G418 (G418 sulfate (GENETICIN), available from GIBCO Company) to a concentration of 600 $\mu$g/ml. Then the cultivation was continued. After 10 days, it was confirmed whether the cells were proliferated or not, 50 $\mu$l of each supernatant was recovered and 50 $\mu$l of a fresh culture medium (10% FCS-containing Ham F-12) was added to the Petri dish.

The E1 protein present in the supernatant was detected by the sandwich ELISA method performed in the usual manner while using an anti-E1 antibody which was obtained by concentrating the supernatant of the recombinant vacurovirus Ac813d-infected Sf9 cells obtained in the step [5], fractionating the concentrate using a GPC column, i.e., AsahipakGS520 (available from Asahi Chemical Industry Co., Ltd.) to give the E1 protein and then immunizing rabbit against the E1 protein as a first antibody, a serum of a patient suffering from C type hepatitis as a secondary antibody and a peroxidase-labeled anti-human goat IgG antibody (Capel Company) as a third antibody.

At the same time, a part of the cells was collected and cultured overnight on Lab-Tek Chamber Slides: Nunc4808 (available from Nippon Intermed Co., Ltd.). The cultured slides were rinsed with phosphate-buffered saline (PBS), immersed in a 1:1 cold acetone/methanol mixture and maintained at −20° C. for 15 minutes to fix the cells to the slides. Then the cells fixed to the slide glasses were reacted with a serum from a C type hepatitis-infected patient diluted 20 times with PBS at 37° C. for 30 minutes. Thereafter, the slide glasses each was washed 3 times (for 5 minutes each) with PBS and reacted with FITC-labeled anti-human rabbit IgG antibody (Daco• Japan Co., Ltd.) diluted 50 times with PBS at 37° C. for 30 minutes. Then the slide glass was washed 3 times (for 5 minutes each) with PBS, sandwiched between two sheets of filter paper to dry it and sealed with glycerin to observe it by a fluorescence microscope.

Thus, the cell line which could perpetually produce the E1 protein was established by continuously repeating three times the limiting dilution-culture procedure while screening positive cells in this manner.

[7] Investigation of Reactivity of the E1 Protein Produced by Insect Cells with Sera from C Type Hepatitis-Infected Patients The polypeptides formed through the expression in the steps [5] and [6] were identified to be C type hepatitis-related antigens since a serum from a C type hepatitis-infected patient immunologically react with these polypeptides. The identification was carried out by the immunoprecipitation technique as will be detailed below. First of all, Sf9 cells were infected with the recombinant virus Ac813d described in the step [5] at 4 PFU/cell, a Grace's culture medium containing 2% dialyzed FCS, methionine in a concentration of 1/20 time the normal concentration and 75 μCi/ml of $^{35}$S-methionine (Amersham Company) was substituted for the medium after 30 hours and the cells were cultured at 27° C. for about 48 hours.

The culture medium was centrifuged at 2,000 rpm for 5 minutes to recover the supernatant. To the labeled E1 protein-containing supernatant (100 μl), there was added 1 μl of a serum from a C type hepatitis-infected patient, followed by reaction at 4° C. for one hour, addition of 10 μl of Protein A Agarose (Pharmacia Company) and additional reaction at 4° C. for one hour. The reaction solution was centrifuged at 15,000 rpm for one minute to remove the Protein A Agarose through precipitation, followed by removal of the supernatant, washing three times with 200 μl of RIPA Buffer (50 mM Tris-HCl, pH 7.5, 0.15 mM NaCl, 0.1% SDS, 1% Triton X-100, 1% sodium deoxycholate) and dissolution thereof in a sample-treating solution for use in SDS-polyacrylamide gel electrophoresis (50 mM Tris-HCl buffer containing 2% SDS, 5% mercaptoethanol, 10% glycerin and 0.005% Bromophenol Blue, pH 6.8).

Then the sample was heated to boiling at 100° C. for 10 minutes. The sample thus prepared (10 μl) was added to a 0.1% SDS-12.5% polyacrylamide gel (70×85×1 mm). At this stage, "LMW Kit E" (a low molecular weight marker protein available from Pharmacia Company) was used as a marker protein. Thus the electrophoresis of the sample was performed at a constant current of 30 mA for about 45 minutes using Tris buffer (25 mM Tris, pH 8.3, 192 mM glycine, 0.1% SDS) as an electrolyte and the sample was stained with Coomassie Brilliant Blue in the usual manner, dried and subjected to autoradiography.

Figure 1:
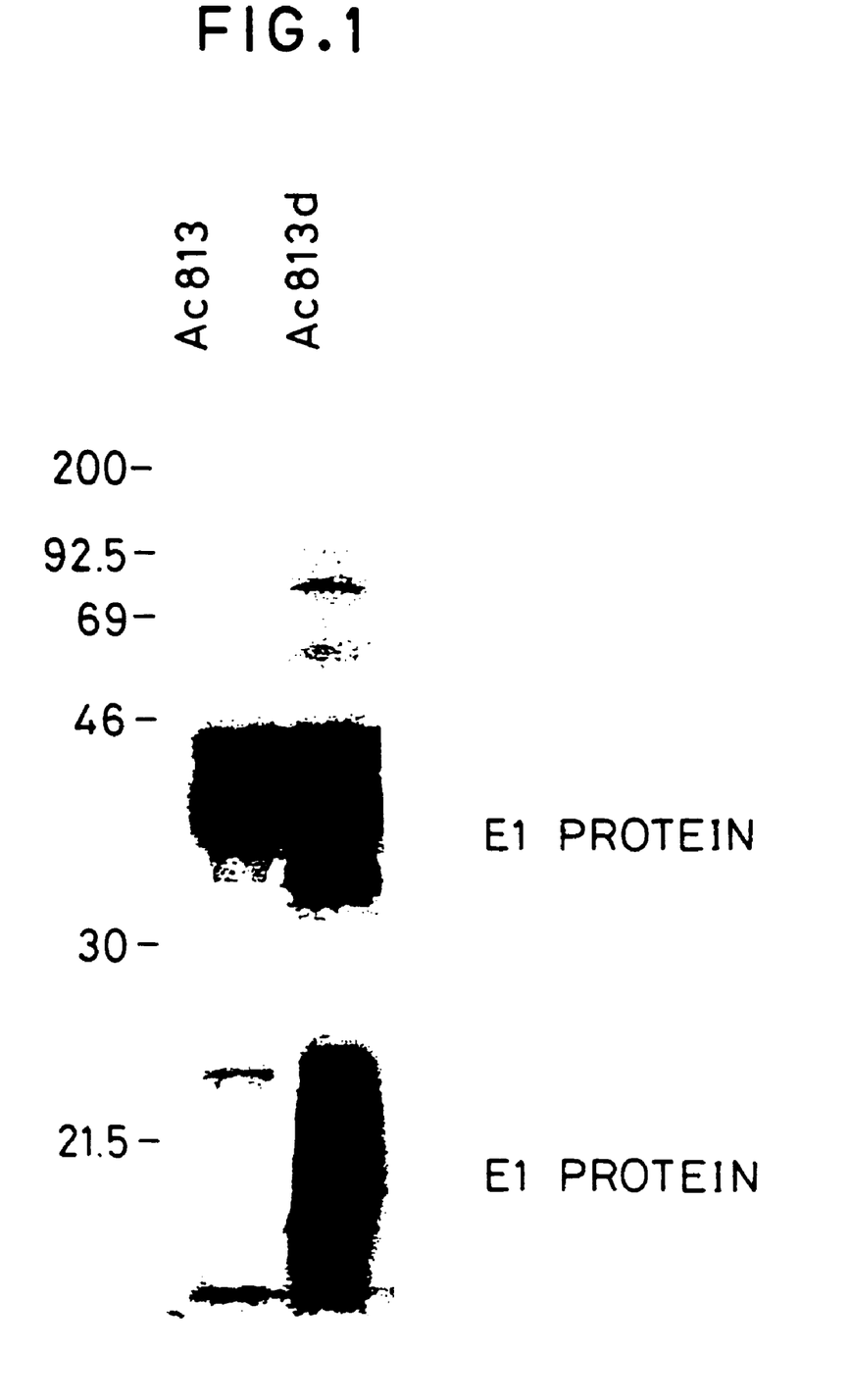
FIG. 1 shows the results observed when a culture supernatant of a recombinant vacurovirus Ac813-infected or vacurovirus Ac813d-infected Sf9 cell is subjected to immunoprecipitation with a serum from a C type hepatitis-infected patient.

[8] Comparison Between the Amounts of E1 Protein (derived from pUC813) and Modified E1 Protein (derived from pUC813d) Expressed and Secreted Sf9 Cells were infected with the recombinant vacurovirus Ac813 in the same manner used in the step [7] and isotope-labeled. The E1 protein present in the resulting culture supernatant was recovered through immunoprecipitation technique and the amount thereof was compared with that observed for Ac813d. As a result, there was observed a substantial difference between the amounts of the expressed E1 proteins as will be seen from FIG. 1.

What is claimed is:

1. An isolated E1 protein of hepatitis C virus, wherein the E1 protein lacks the amino acid segment represented by amino acids 263 to 289 of SEQ ID NO: 2.

2. The isolated E1 protein of claim 1, wherein the E1 protein is encoded by Ac813d.

3. An isolated E1 protein of hepatitis C virus, wherein the E1 protein lacks the amino acid segment represented by amino acids 263 to 289 of SEQ ID NO: 2, wherein the E1 protein is produced by the steps of:

(a) transforming a host with an expression vector containing a DNA fragment encoding the E1 protein;

(b) cultivating the transformant, thereby causing the E1 protein to be produced and secreted; and (c) recovering the E1 protein.

4. The isolated E1 protein of claim 3, wherein the host is an insect cell or an animal cell.

5. The isolated E1 protein of claim 3, wherein the E1 protein is encoded by Ac813d.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1037 base pairs
      (B) TYPE: nucleic acid
      (C) STRANDEDNESS: double
      (D) TOPOLOGY: linear    (ii) MOLECULE TYPE: DNA (genomic)

(iv) ANTI-SENSE: NO

(vi) ORIGINAL SOURCE:
      (A) ORGANISM: Hepatitis C virus    (vii) IMMEDIATE SOURCE:
      (B) CLONE: pUC010

(ix) FEATURE:
      (A) NAME/KEY: CDS
      (B) LOCATION: 17..1036

-continued (xi) SEQUENCE DESCRIPTION: SEQ ID NO:1:

```
CTGCAGACCG TGCATC ATG AGC ACA AAT CCT AAA CCC CAA AGA AAA ACC          49
                  Met Ser Thr Asn Pro Lys Pro Gln Arg Lys Thr
                    1               5                  10

AAA CGT AAC ACC AAC CGT CGC CCA CAG GAC GTT AAG TTC CCG GGC GGT         97
Lys Arg Asn Thr Asn Arg Arg Pro Gln Asp Val Lys Phe Pro Gly Gly
            15                  20                  25

GGT CAG ATC GTC GGT GGA GTT TAC TTG TTG CCG CGC AGG GGC CCC AGG        145
Gly Gln Ile Val Gly Gly Val Tyr Leu Leu Pro Arg Arg Gly Pro Arg
        30                  35                  40

TTG GGT GTG CGT GCG ACT AGG AAG ACT TCC GAG CGG TCG CAA CCT CGT        193
Leu Gly Val Arg Ala Thr Arg Lys Thr Ser Glu Arg Ser Gln Pro Arg
    45                  50                  55

GGA AGG CGA CAA CCT ATC CCC AAG GCT CGC CGG CCC GAG GGC AGG ACC        241
Gly Arg Arg Gln Pro Ile Pro Lys Ala Arg Arg Pro Glu Gly Arg Thr
60                  65                  70                  75

TGG GCT CAG CCT GGG TAT CCT TGG CCC CTC TAT GGC AAT GAG GGC TTG        289
Trp Ala Gln Pro Gly Tyr Pro Trp Pro Leu Tyr Gly Asn Glu Gly Leu
                80                  85                  90

GGG TGG GCA GGA TGG CTC CTG TCA CCC CGC GGC TCT CGG CCT AGT TGG        337
Gly Trp Ala Gly Trp Leu Leu Ser Pro Arg Gly Ser Arg Pro Ser Trp
            95                 100                 105

GGC CCT AAT GAC CCC CGG CGT AGG TCG CGT AAT TTG GGT AAG GTC ATC        385
Gly Pro Asn Asp Pro Arg Arg Ser Arg Asn Leu Gly Lys Val Ile
        110                 115                 120

GAT ACC CTT ACA TGC GGC TTC GCC GAC CTC ATG GGG TAC ATC CCG CTT        433
Asp Thr Leu Thr Cys Gly Phe Ala Asp Leu Met Gly Tyr Ile Pro Leu
    125                 130                 135

GTC GGC GCC CCC TTA GGG GGC GCT GCC AGG GCC CTG GCA CAT GGT GTC        481
Val Gly Ala Pro Leu Gly Gly Ala Ala Arg Ala Leu Ala His Gly Val
140                 145                 150                 155

CGG GTT CTG GAG GAC GGC GTG AAC TAT GCA ACA GGG AAT TTG CCC GGT        529
Arg Val Leu Glu Asp Gly Val Asn Tyr Ala Thr Gly Asn Leu Pro Gly
                160                 165                 170

TGC TCT TTC TCT ATC TTC CTC TTA GCT CTG CTG TCC TGT TTG ACC ATC        577
Cys Ser Phe Ser Ile Phe Leu Leu Ala Leu Leu Ser Cys Leu Thr Ile
            175                 180                 185

CCA GCT TCC GCT TAT GAA GTG CGC AAC GTG TCC GGG ATA TAC CAT GTC        625
Pro Ala Ser Ala Tyr Glu Val Arg Asn Val Ser Gly Ile Tyr His Val
        190                 195                 200

ACA AAC GAC TGC TCC AAC TCA AGC ATT GTG TAT GAG GCG GCG GAC GTG        673
Thr Asn Asp Cys Ser Asn Ser Ser Ile Val Tyr Glu Ala Ala Asp Val
    205                 210                 215

ATC ATG CAT GCC CCC GGG TGC GTG CCC TGC GTT CGG GAG AAC AAT TCC        721
Ile Met His Ala Pro Gly Cys Val Pro Cys Val Arg Glu Asn Asn Ser
220                 225                 230                 235

TCC CGT TGC TGG GTA GCG CTC ACT CCC ACG CTC GCG GCC AGG AAT GCC        769
Ser Arg Cys Trp Val Ala Leu Thr Pro Thr Leu Ala Ala Arg Asn Ala
                240                 245                 250

AGC GTC CCC ACT ACG ACA TTA CGA CGC CAC GTC GAC TTG CTC GTT GGG        817
Ser Val Pro Thr Thr Thr Leu Arg Arg His Val Asp Leu Leu Val Gly
            255                 260                 265

ACG GCT GCT TTC TGC TCC GCT ATG TAC GTG GGG GAT CTC TGC GGA TCT        865
Thr Ala Ala Phe Cys Ser Ala Met Tyr Val Gly Asp Leu Cys Gly Ser
        270                 275                 280

GTT TTC CTC ATC TCC CAG CTG TTC ACC TTC TCG CCT CGC CGG CAT GAG        913
Val Phe Leu Ile Ser Gln Leu Phe Thr Phe Ser Pro Arg Arg His Glu
    285                 290                 295

ACA GTA CAG GAC TGC AAC TGC TCA ATC TAT CCC GGC CAC GTA TCA GGC        961
Thr Val Gln Asp Cys Asn Cys Ser Ile Tyr Pro Gly His Val Ser Gly
```

```
Thr Val Gln Asp Cys Asn Cys Ser Ile Tyr Pro Gly His Val Ser Gly
300                 305                 310                 315

CAT CGT ATG GCT TGG GAT ATG ATG ATG AAC TGG TCG CCC ACG GCA GCC      1009
His Arg Met Ala Trp Asp Met Met Met Asn Trp Ser Pro Thr Ala Ala
                320                 325                 330

TTA GTG GTG TCG CAG TTA CTC CGG ATC C                                1037
Leu Val Val Ser Gln Leu Leu Arg Ile
                335                 340

(2) INFORMATION FOR SEQ ID NO:2:

(i) SEQUENCE CHARACTERISTICS:
        (A) LENGTH: 340 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Ile Tyr His Val Thr Asn Asp Cys Ser
        195                 200                 205

Asn Ser Ser Ile Val Tyr Glu Ala Ala Asp Val Ile Met His Ala Pro
210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Leu Arg Arg His Val Asp Leu Leu Val Gly Thr Ala Ala Phe Cys
            260                 265                 270

Ser Ala Met Tyr Val Gly Asp Leu Cys Gly Ser Val Phe Leu Ile Ser
        275                 280                 285

Gln Leu Phe Thr Phe Ser Pro Arg Arg His Glu Thr Val Gln Asp Cys
290                 295                 300
```

```
Asn Cys Ser Ile Tyr Pro Gly His Val Ser Gly His Arg Met Ala Trp
305                 310                 315                 320

Asp Met Met Met Asn Trp Ser Pro Thr Ala Ala Leu Val Val Ser Gln
            325                 330                 335

Leu Leu Arg Ile
            340

(2) INFORMATION FOR SEQ ID NO:3:

(i) SEQUENCE CHARACTERISTICS:
        (A) LENGTH: 1037 base pairs
        (B) TYPE: nucleic acid
        (C) STRANDEDNESS: double
        (D) TOPOLOGY: linear (ii) MOLECULE TYPE: DNA (genomic)

(iv) ANTI-SENSE: NO (vi) ORIGINAL SOURCE:
         (A) ORGANISM: Hepatitis C virus (vii) IMMEDIATE SOURCE:
          (B) CLONE: pUCM010

(ix) FEATURE:
         (A) NAME/KEY: CDS
         (B) LOCATION: 17..1036

(xi) SEQUENCE DESCRIPTION: SEQ ID NO:3:

CTGCAGACCG TGCATC ATG AGC ACA AAT CCA AAA CCC CAA AGA AAA ATC            49
               Met Ser Thr Asn Pro Lys Pro Gln Arg Lys Ile
                 1               5                  10

AAA CGT AAC ACC AAC CGC CGC CCA CAG GAC GTT AAG TTC CCG GGC GGT          97
Lys Arg Asn Thr Asn Arg Arg Pro Gln Asp Val Lys Phe Pro Gly Gly
             15                  20                  25

GGT CAG ATC GTT GGT GGA GTT TAC CTG TTG CCG CGC AGG GGC CCC AGG         145
Gly Gln Ile Val Gly Gly Val Tyr Leu Leu Pro Arg Arg Gly Pro Arg
         30                  35                  40

TTG GGT GTG CGC GCG ACT AGG AAG ACT TCC GAG CGG CCG CAA CCT CGT         193
Leu Gly Val Arg Ala Thr Arg Lys Thr Ser Glu Arg Pro Gln Pro Arg
     45                  50                  55

GGA AGG CGA CAA CCT ATC CCC AAG GCT CGC CAA CCC GAG GGT AGG GCC         241
Gly Arg Arg Gln Pro Ile Pro Lys Ala Arg Gln Pro Glu Gly Arg Ala
 60                  65                  70                  75

TGG GCT CAG CCC GGG TAC CCT TGG CCC CTC TAT GGC AAT GAG GGC TTG         289
Trp Ala Gln Pro Gly Tyr Pro Trp Pro Leu Tyr Gly Asn Glu Gly Leu
                 80                  85                  90

GGG TGG GCA GGA TGG CTC CTG TCA CCC CGC GGC TCC CGG CCT AGT TGG         337
Gly Trp Ala Gly Trp Leu Leu Ser Pro Arg Gly Ser Arg Pro Ser Trp
             95                 100                 105

GGC CCC ACG GAC CCC CGG CGT AGG TCG CGT AAT TTG GGT AAG GTC ATC         385
Gly Pro Thr Asp Pro Arg Arg Arg Ser Arg Asn Leu Gly Lys Val Ile
         110                 115                 120

GAT ACC CTC ACA TGC GGC TTC GCC GAC CTC ATG GGG TAC ATT CCG CTC         433
Asp Thr Leu Thr Cys Gly Phe Ala Asp Leu Met Gly Tyr Ile Pro Leu
     125                 130                 135

GTC GGC GCC CCC CTA GGG GGC GCT GCC AGG GCT CTA GCG CAT GGC GTC         481
Val Gly Ala Pro Leu Gly Gly Ala Ala Arg Ala Leu Ala His Gly Val
140                 145                 150                 155

CGG GTT CTG GAG GAC GGC GTG AAC TAT GCA ACA GGG AAT CTG CCT GGT         529
Arg Val Leu Glu Asp Gly Val Asn Tyr Ala Thr Gly Asn Leu Pro Gly
                 160                 165                 170
```

```
TGC TCC TTT TCT ATC TTC CTT TTG GCT TTG CTG TCC TGT TTG ACC ATC        577
Cys Ser Phe Ser Ile Phe Leu Leu Ala Leu Leu Ser Cys Leu Thr Ile
            175                 180                 185

CCA GCT TCC GCC TAC CAA GTG CGC AAC GCG TCC GGG GTG TAC CAT GTC        625
Pro Ala Ser Ala Tyr Gln Val Arg Asn Ala Ser Gly Val Tyr His Val
            190                 195                 200

ACG AAC GAC TGC TCC AAC TCA AGT ATT GTG TAT GAG GCG GCG GAC GTG        673
Thr Asn Asp Cys Ser Asn Ser Ser Ile Val Tyr Glu Ala Ala Asp Val
            205                 210                 215

ATT ATG CAC ACC CCC GGG TGC GTG CCC TGC GTC CGG GAG AAC AAT TCC        721
Ile Met His Thr Pro Gly Cys Val Pro Cys Val Arg Glu Asn Asn Ser
220             225                 230                 235

TCC CGC TGC TGG GTA GCG CTC ACT CCC ACG CTT GCG GCC AGG AAC AGC        769
Ser Arg Cys Trp Val Ala Leu Thr Pro Thr Leu Ala Ala Arg Asn Ser
                240                 245                 250

AGC ATC CCC ACT ACG ACA ATA CGG CGT CAT GTC GAC TTG CTC GTT GGG        817
Ser Ile Pro Thr Thr Thr Ile Arg Arg His Val Asp Leu Leu Val Gly
                    255                 260                 265

GCA GCT GCT CTC TGT TCC GCT ATG TAT GTG GGG GAT TTT TGC GGA TCT        865
Ala Ala Ala Leu Cys Ser Ala Met Tyr Val Gly Asp Phe Cys Gly Ser
                    270                 275                 280

GTT TTC CTC GTC TCC CAG CTG TTC ACT TTC TCA CCT CGC CGG TAT GAG        913
Val Phe Leu Val Ser Gln Leu Phe Thr Phe Ser Pro Arg Arg Tyr Glu
            285                 290                 295

ACG GTG CAA GAC TGC AAT TGC TCA ATC TAT CCC GGC CAT GTA TCA GGC        961
Thr Val Gln Asp Cys Asn Cys Ser Ile Tyr Pro Gly His Val Ser Gly
300             305                 310                 315

CAT CGC ATG GCT TGG GAT ATG ATA ATG AAT TGG TCA CCT ACA ACA GCC       1009
His Arg Met Ala Trp Asp Met Ile Met Asn Trp Ser Pro Thr Thr Ala
                320                 325                 330

CTA GTG GTA TCG CAG CTA CTC CGG ATC C                                 1037
Leu Val Val Ser Gln Leu Leu Arg Ile
            335                 340
```

(2) INFORMATION FOR SEQ ID NO:4:

(i) SEQUENCE CHARACTERISTICS:
        (A) LENGTH: 340 amino acids
        (B) TYPE: amino acid
        (D) TOPOLOGY: linear     (ii) MOLECULE TYPE: protein     (xi) SEQUENCE DESCRIPTION: SEQ ID NO:4:

```
Met Ser Thr Asn Pro Lys Pro Gln Arg Lys Ile Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Pro Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125
```

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Gln Val Arg Asn Ala Ser Gly Val Tyr His Val Thr Asn Asp Cys Ser
        195                 200                 205

Asn Ser Ser Ile Val Tyr Glu Ala Ala Asp Val Ile Met His Thr Pro
210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ser Ser Ile Pro Thr Thr
                245                 250                 255

Thr Ile Arg Arg His Val Asp Leu Leu Val Gly Ala Ala Ala Leu Cys
            260                 265                 270

Ser Ala Met Tyr Val Gly Asp Phe Cys Gly Ser Val Phe Leu Val Ser
        275                 280                 285

Gln Leu Phe Thr Phe Ser Pro Arg Arg Tyr Glu Thr Val Gln Asp Cys
    290                 295                 300

Asn Cys Ser Ile Tyr Pro Gly His Val Ser Gly His Arg Met Ala Trp
305                 310                 315                 320

Asp Met Ile Met Asn Trp Ser Pro Thr Thr Ala Leu Val Val Ser Gln
                325                 330                 335

Leu Leu Arg Ile
            340

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CGGGATCCGG AGTAACTGCG                                                   20

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CGCTGCAGAC CGTGCATCAT GAGCAC                                            26

(2) INFORMATION FOR SEQ ID NO:7:

(i) SEQUENCE CHARACTERISTICS:
        (A) LENGTH: 17 base pairs
        (B) TYPE: nucleic acid -continued

```
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTAAAACGAC GGCCAGT                                                    17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CAGGAAACAG CTATGAC                                                    17

(2) INFORMATION FOR SEQ ID NO:9:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AGCGGCCGCT                                                            10
```